United States Patent
Rizvi

[11] Patent Number: 6,120,438
[45] Date of Patent: Sep. 19, 2000

[54] POSTERIOR VAGINAL RETRACTOR FOR VAGINAL SURGERY OR PROCEDURE

[76] Inventor: Syed Rizvi, 6208 Castle Cary Dr., Bakersfld, Calif. 93306

[21] Appl. No.: 09/451,544

[22] Filed: Dec. 1, 1999

[51] Int. Cl.[7] ................................................ A61B 1/32
[52] U.S. Cl. ............................................ 600/228; 600/235
[58] Field of Search ....................... 600/201, 227, 600/228, 229, 231, 235

[56] References Cited

U.S. PATENT DOCUMENTS

| | | | |
|---|---|---|---|
| 605,547 | 6/1898 | Holland | 600/227 X |
| 1,030,530 | 6/1912 | Palmer | 600/227 X |
| 2,374,863 | 5/1945 | Guttmann. | |
| 3,709,215 | 1/1973 | Richmond. | |

FOREIGN PATENT DOCUMENTS 179309  11/1906  Germany ................................ 600/201

*Primary Examiner*—Jeffrey A. Smith
*Attorney, Agent, or Firm*—Donald A. Kettlestrings

[57] ABSTRACT

A posterior vaginal retractor for vaginal surgery or procedure includes a flat plate member, a support member connected to the plate member, an arm member vertically adjustably connected to the support member, and a speculum member connected to the arm member. The plate member is positioned under the female patient's buttocks when the patient is on the operating table with legs up. The speculum member is inserted into the vagina, and the position of the speculum member is vertically adjusted to a desired fixed position by vertically moving the arm member so that the speculum member will depress the posterior wall of the vagina to facilitate a vaginal procedure or surgery.

12 Claims, 2 Drawing Sheets

POSTERIOR VAGINAL RETRACTOR FOR VAGINAL SURGERY OR PROCEDURE

BACKGROUND OF THE INVENTION

This invention relates to a vaginal retractor and more particularly to a posterior vaginal retractor for vaginal procedures or surgery.

The use of weighted speculums is well known for depressing the posterior vaginal wall of patients during surgery or other procedures. However, weighted speculums move, slip and fall onto the floor or onto the surgeon's feet. They are either too short or too long and constantly slip and fall. The angle of the weighted speculum blade is either too sharp and consequently obstructs the surgeon's view, or the angle of the blade is too shallow to stay in the vagina during the surgery or procedure.

Blades of weighted speculums do not conform to the shape of the vagina, and they are not heavy enough to depress the posterior vaginal wall in patients with strong perineal muscles. Also, with weighted speculums, the level of depression of the posterior vaginal wall is not under the surgeon's control. As a result, the surgeon cannot control the view required to perform any particular procedure. Heavy weighted speculums come in standard sizes and do not meet the need for different patient sizes, particularly in children. All of these factors adversely affect the quality of the surgery or the procedure, increase surgery time, contribute to the surgeon's frustration, and increase the cost of the surgery or the procedure and the risk of complications.

It is, therefore, an object of the present invention to provide a posterior vaginal retractor which enables a surgeon to perform vaginal surgeries or procedures under a controlled environment with ease and with avoidance of the factors described above.

Another object is to provide a posterior vaginal retractor for vaginal surgeries or procedures which offers versatility and flexibility to the surgeon together with more control over the surgery or procedure.

A further object of the invention is the provision of a posterior vaginal retractor which fixes a speculum blade in one desired position so that the blade does not move, slip or fall.

Still another object is to provide a posterior vaginal retractor which can be used with the lower blade of any standard or conventional vaginal speculum.

A still further object is to provide a posterior vaginal retractor which enables the surgeon to fix the posterior vaginal wall in any position desired by the surgeon to perform a surgery or procedure.

Still another object is to provide a posterior vaginal retractor which provides an enhanced view of the vagina during the surgery or procedure and which also provides a better view of pedicles to assist in prevention, early diagnosis and treatment of bleeding from the pedicles, thus reducing the risk of complications.

Another object is to provide a posterior vaginal retractor all parts of which are fixed in a desired position during use so there is no risk of instruments falling and injuring the surgeon or a surgical assistant.

Another object is to provide a posterior vaginal retractor which allows the assistant more opportunity to attend to other events and steps during the surgery or the procedure.

A further object of the invention is the provision of a posterior vaginal retractor which enables the surgeon to pay more attention to the actual surgery or procedure and allows the surgeon to respond quickly and effectively in handling complications.

Another object is to provide a posterior vaginal retractor which can be used with specially designed speculum blades to provide greater ease and flexibility for certain vaginal procedures.

Additional objects and advantages of the invention will be set forth in part in the description which follows, and in part will be obvious from the description, or may be learned by practice of the invention. The objects and advantages are realized and attained by means of the instrumentalities and combinations particularly pointed out in the appended claims.

SUMMARY OF THE INVENTION

To achieve these and other objects, the present invention provides a posterior vaginal retractor for vaginal surgeries or procedures which includes a flat plate member; a support member connected to the plate member; an arm member vertically adjustably connected to the support member; and a speculum member connected to the arm member.

It is to be understood that both the foregoing general description and the following detailed description are exemplary and explanatory but are not restrictive of the invention.

BRIEF DESCRIPTION OF THE DRAWINGS

The accompanying drawings, which are incorporated in and constitute a part of this specification, illustrate a preferred embodiment of the invention and, together with the description, serve to explain the principles of the invention.

DESCRIPTION OF THE PREFERRED EMBODIMENT

Figure 1:
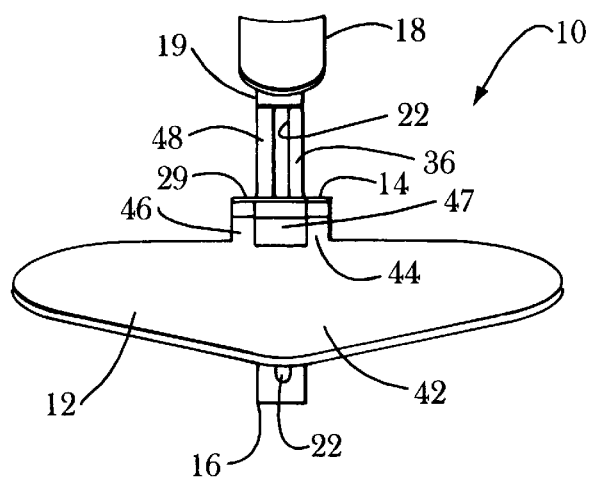
FIG. 1 is a front perspective view of the retractor.

With reference now to the drawings, wherein like reference characters designate like or corresponding parts throughout the several views, there is shown a posterior vaginal retractor 10 which includes a flat plate member 12. A support member 14 is connected to plate member 12, and an arm member 16 is vertically adjustably connected to support member 14. A speculum member or blade 18 is connected to arm member 16.

Support member 14 includes a first pin member 20, and arm member 16 defines an elongated slot 22 for slidably receiving pin member 20 therein when arm member 16 is vertically adjustably connected to support member 14.

Speculum member or blade 18 includes a second pin member 24, and arm member 16 defines an opening 26 for receiving pin member 24 therein when speculum member or blade 18 is connected to arm member 16.

Support member 14 includes first and second opposed guide elements 28, 28' positioned for slidably receiving arm member 16 therebetween.

Arm member 16 includes a handle element 30 for grasping by a user. Arm member 16 further defines an angled portion 32 between opening 26 and slot 22 for enhancing the downward range of movement of arm member 16 and speculum member or blade 18 in relationship with respect to support member 14.

In accordance with the invention, arm member 16 defines a first portion 34 containing opening 26 therein and a second portion 36 containing slot 22 therein, and portions 34, 36 are oriented in parallel relationship with each other.

Pin members 20, 24 are each externally threaded, and nut elements, such as wing nuts, 38, 40 are provided for threadable and removable attachment to pin members 20, 24, respectively.

Plate member 12 preferably includes a first triangular plate portion 42, a second plate portion 44 extending from first plate portion 42, and a third plate portion 46 extending from first plate portion 42 and in parallel, spaced-apart relationship with second plate portion 44. Support member 14 is connected to and extends upwardly from plate portions 44, 46.

Portion 36 of arm member 16 defines first and second opposed and parallel side surfaces 48, 48', and angled portion 32 extends in a direction to create an obtuse angle 50 with first side surface 48. Handle element 30 extends outwardly away from second side surface 48' of arm member 16.

In operation and use, first plate portion 42 is positioned under the female patient's buttocks when the patient is on the operating table with legs up. Speculum member or blade 18 is inserted into the patient's vagina, and the position of speculum member or blade 18 is vertically adjusted to a desired fixed position by vertically moving arm member 16 so that speculum member or blade 18 will depress the posterior wall of the vagina to facilitate a vaginal procedure or surgery.

Speculum member or blade 18 is connected to arm member 16 by positioning second pin member 24 through opening 26 and by threading nut element 40 onto pin member 24 so that speculum member or blade 18 is fixedly attached to arm member 16.

Arm member 16 is vertically, adjustably connected to support member 14 by positioning first pin member 20 through elongated slot 22 and by slidably positioning arm member 16 between guide elements 28, 28'.

Figure 2:
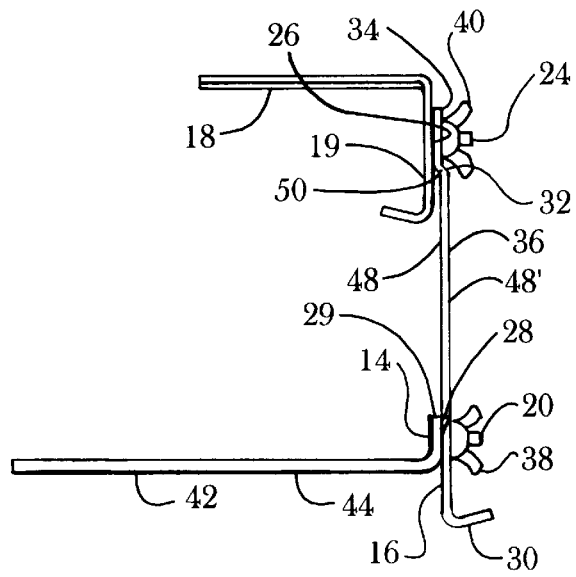
FIG. 2 is a side elevation view of the retractor.
Figure 3:
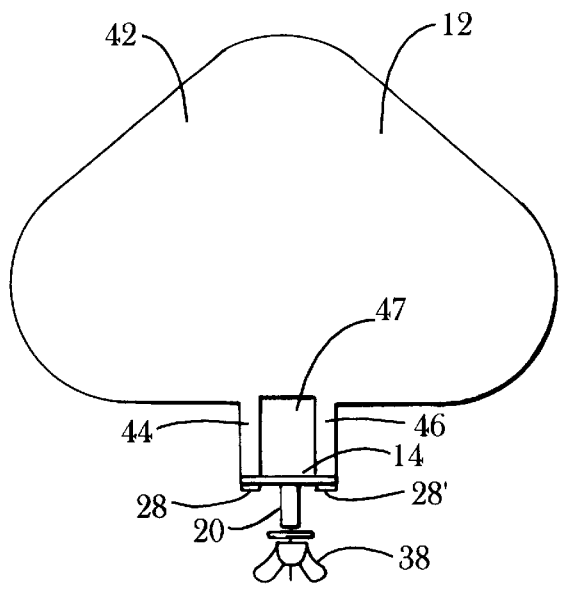
FIG. 3 is a top plan view of plate member 12 of the retractor.
Figure 4:
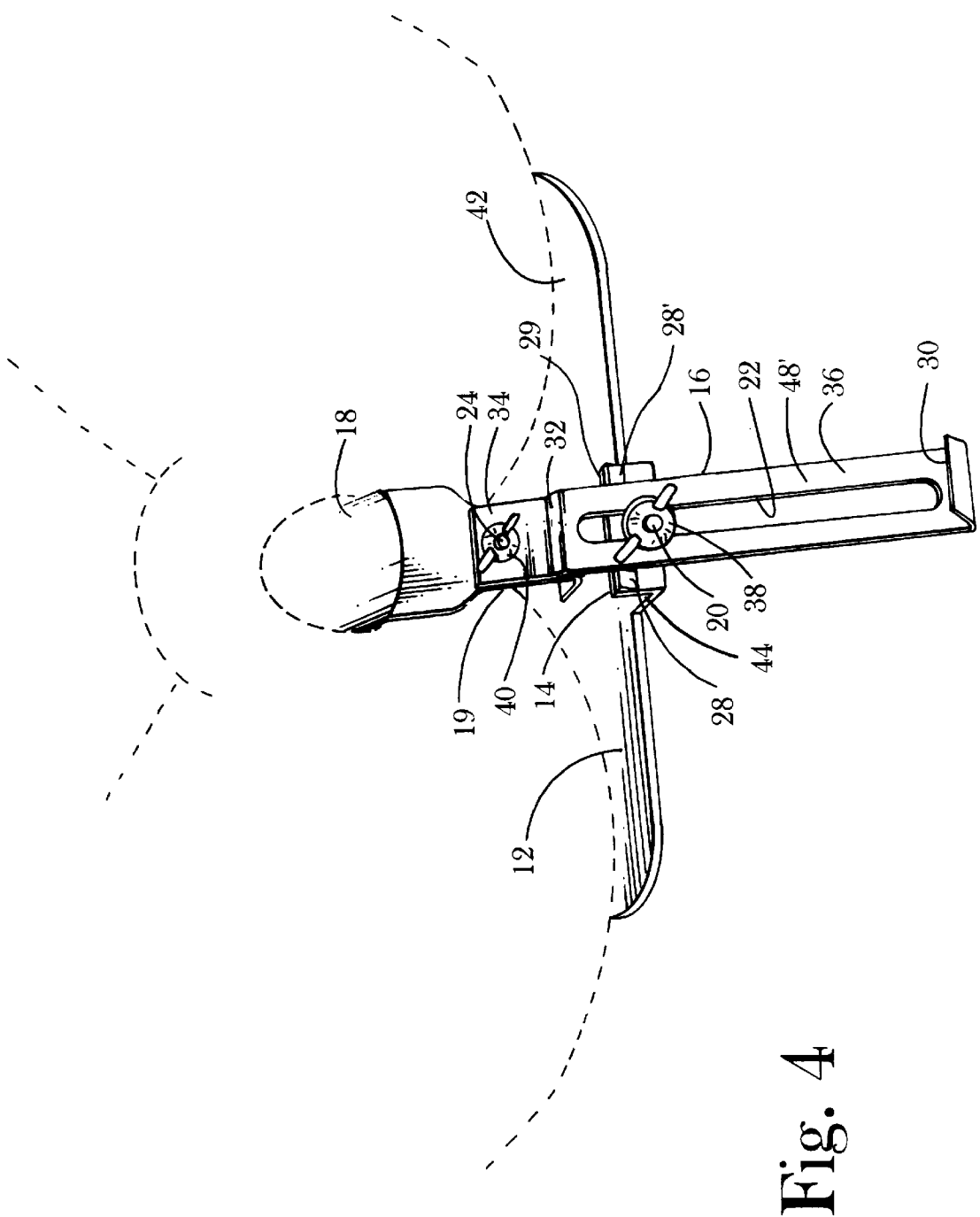
FIG. 4 is a perspective view, partially in phantom, showing the retractor in use.

Speculum member or blade 18 is connected to arm member 16 to project from first side surface 48, and arm member 16 is adjustably connected to support member 14 with handle element 30 projecting from second side surface 48' and in a direction away from support 14. See FIG. 2.

The positions of speculum member or blade 18 and arm 16 are vertically adjusted by vertically sliding pin member 20 along slot 22 until speculum member or blade 18 depresses the posterior wall of the vagina in the manner desired. Nut element 38 is then tightened onto pin member 20 and against arm member 16 to fixedly position arm member 16 and speculum member or blade 18 in the desired location.

The configuration of arm member 16, which includes angled portion 32, enhances the downward range of movement of arm member 16 and speculum member or blade 18 in relationship with respect to support member 14. Specifically, angled portion 32 of arm member 16 enables speculum member or blade 18 to move downwardly past upper portion or edge 29 of support member 14 and into space 47 between plate portions 44, 46. The width of speculum member 18 at lower portion 19 is less than the distance between plate portions 44, 46 to enable speculum member 18 to be moved downwardly between plate portions 44, 46.

Retractor 10 is preferably comprised of stainless steel, and retractor 10 can be used for any vaginal procedure in any patient. Speculum member or blade 18 can be any standard vaginal speculum or can be a specially designed blade for certain vaginal procedures.

Retractor 10 enables the surgeon to fix the posterior vaginal wall in any position required by the surgeon to perform the surgery or procedure. It fixes speculum member or blade 18 in one fixed position so that the blade does not move, slip or fall. During vaginal hysterectomy, the speculum member or blade 18 can be introduced into the posterior cul-de-sac, assisting the surgeon with clamping of the uterosacral, cardinal, broad and infundibulopelvic ligaments and assisting with the delivery of the uterus.

Retractor 10 not only provides a better view of the vagina but also provides a better view of pedicles so as to assist in prevention, early diagnosis and treatment of bleeding from the pedicles to reduce risk of complications. During use, all parts of retractor 10 are fixed in desired positions so there is no risk of instruments falling and injuring the surgeon, the assistant or the patient.

The invention in its broader aspects is not limited to the specific details shown and described, and departures may be made from such details without departing from the principles of the invention and without sacrificing its chief advantages.

What is claimed is:

1. A posterior vaginal retractor, comprising:

a substantially flat plate member;

a support member connected to said plate member;

an arm member adjustably connected to said support member;

a speculum member connected to said arm member; and wherein said support member includes a first pin member and wherein said arm member defines an elongated slot for slidably receiving said first pin member therein when said arm member is adjustably connected to said support member.

2. A retractor as in claim 1 wherein said speculum member includes a second pin member and wherein said arm member defines an opening for receiving said second pin member therein when said speculum member is connected to said arm member.

3. A retractor as in claim 2 wherein said support member includes first and second guide elements positioned for slidably receiving said arm member therebetween.

4. A retractor as in claim 3 wherein said arm member includes a handle element for grasping by a user.

5. A retractor as in claim 4 wherein said arm member defines an angled portion between said opening and said slot for enhancing downward range of movement of said arm member and said speculum member in relationship with said support member.

6. A retractor as in claim 5 wherein said arm member defines a first portion containing said opening therein and a second portion containing said slot therein and wherein said first and second portions are in substantially parallel relationship with each other.

7. A retractor as in claim 6 wherein said first and second pin members are externally threaded and wherein said retractor further includes first and second nut elements for threadable and removable attachment to said first and second pin members, respectively.

8. A retractor as in claim 7 wherein said plate member includes:

a first plate portion;

a second plate portion extending from said first plate portion;

a third plate portion extending from said first plate portion and in spaced-apart relationship with said second plate portion; and wherein said support member is connected to and extends upwardly from said second and third plate portions.

9. A retractor as in claim 8 wherein said second portion of said arm member defines first and second opposed and substantially parallel side surfaces and wherein said angled portion extends in a direction to create an obtuse angle with said first side surface.

10. A retractor as in claim 9 wherein said handle element extends outwardly away from said second side surface.

11. A retractor as in claim 10 wherein said second plate portion and said third place portion are spaced apart from each other by at least a first predetermined distance, and wherein said speculum member defines a lower portion width less than said first predetermined distance for enabling said speculum member to be moved downwardly between said second and third plate portions.

12. A posterior vaginal retractor, comprising:

a substantially flat plate member;

a support member connected to said plate member;

an arm member normally vertically adjustably connected to said support member; and a speculum member connected to said arm member.

* * * * *